United States Patent [19]

Giantureo et al.

[11] Patent Number: 5,035,706
[45] Date of Patent: Jul. 30, 1991

[54] PERCUTANEOUS STENT AND METHOD FOR RETRIEVAL THEREOF

[75] Inventors: Cesare Giantureo, Champaign, Ill.; Thomas A. Osborne, Bloomington, Ind.

[73] Assignee: Cook Incorporated, Bloomington, Ind.

[21] Appl. No.: 422,606

[22] Filed: Oct. 17, 1989

[51] Int. Cl.$^5$ .......................................... A61M 29/00
[52] U.S. Cl. ..................................................... 606/198
[58] Field of Search ............... 606/108, 153, 154, 155, 606/156, 198, 200, 191; 604/105, 106

[56] References Cited

U.S. PATENT DOCUMENTS

| | | | |
|---|---|---|---|
| 3,771,526 | 11/1973 | Rudie | 606/153 |
| 4,214,587 | 7/1980 | Sakura | 606/155 |
| 4,535,770 | 8/1985 | Lemole | 606/108 |

Primary Examiner—Michael H. Thaler
Attorney, Agent, or Firm—Woodard, Emhardt, Naughton, Moriarty & McNett

[57] ABSTRACT

A self-expanding stent formed of stainless steel wire arranged in a closed zig-zag configuration includes an endless series of straight sections joined at their ends by bends. The stent is compressible into a reduced diameter size for insertion into and removal from a body passageway. The bends of at least one end of the stent are formed into eyes for connection with the eyes at one end of a similarly constructed stent to permit single-step introduction of several lengths of stent into the passageway. A stent can include a monofilament thread passing through successive eyes at one end of the stent, the thread passing through each eye at least once and through some of the eyes a second time. The trailing ends of the thread extend from the stent and outside the body passageway. The stent can be retrieved from the body passageway by threading a tube of the free ends of the thread until the tube is adjacent the stent. The diameter at one end of the stent is reduced by pulling the free ends of the thread through the tube. A sheath concentrically disposed over the tube is introduced into the body passageway and over the remaining length of the stent to further compress the stent for removal from the passageway.

12 Claims, 4 Drawing Sheets

PERCUTANEOUS STENT AND METHOD FOR RETRIEVAL THEREOF

BACKGROUND OF THE INVENTION

This invention relates to stents and a method for retrieving stents after insertion into the body of a patient. In particular, the invention relates to modifications to the Gianturco Expandable Wire Stent.

It is desirable in various situations to provide means for expanding a constricted vessel portion or for maintaining an open passageway through a vessel portion. Such situations arise, for example, in conjunction with arteriosclerosis that restricts or stops blood flow through a vessel, or in conjunction with diseases of the prostrate gland which resrict or stop flow through the urethra.

Figure 1:
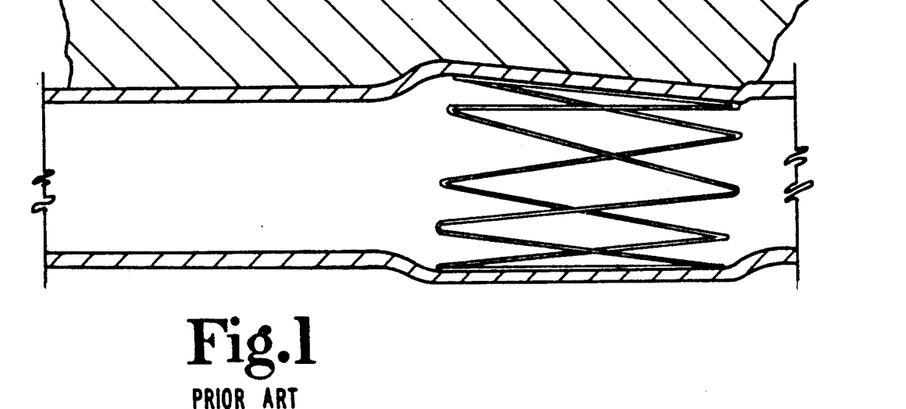
FIG. 1 is side cross-sectional view of a body passageway with a self-expanding wire stent of the prior art situated therein.

A percutaneous stent developed by Dr. Cesare Gianturco is formed of a stainless steel wire arranged in a closed, zig-zag pattern, as more fully described in U.S. Pat. No. 4,580,568. The Gianturco stent, or the Z-stent as it is also known, is compressed into a reduced size shape with an outer diameter which is many times smaller its outer diameter in an expanded shape. The stent is positioned in a passageway by means of a sheath while the stent is retained in the compressed reduced size shape. A pusher or flat-ended catheter is used through the sheath to hold the stent in place in the passageway while the sheath is withdrawn, thereby allowing the stent to expand in the passageway into its expanded shape to hold the passageway open and enlarged. Thus, the Z-stent provides a self-expanding means for maintaining an open passageway. FIG. 1 illustrates the use of the well-known Z-stent wire within a body passageway.

Figure 2:
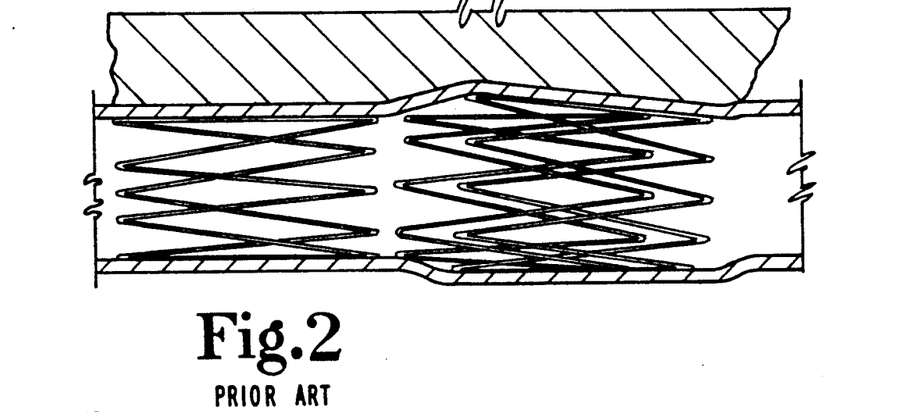
FIG. 2 is a view similar to FIG. 1 showing the use of several stents of the prior art within the body passageway.

FIG. 2 illustrates the use of several Z-stents along a limited length of a body passageway. In illustrated arrangement, two stents are situated in an overlapping arrangement, while a third stent is disposed slightly downstream from the other two stents. As discussed more fully in the above-referenced Gianturco '568 patent, each of the three stents must be separately inserted using the sheath and pusher described above.

Since the initial development of the expandable wire Z-stent, it has been discovered that over time a Z-stent may continue to expand to its maximum diameter even though it was originally deployed in a passageway that had a diameter somewhat smaller than the maximum outer diameter of the expanded stent. Thus, the end result has been in some cases that the stent becomes embedded deeply into the walls of the passageway. In an effort to address this particular problem, others in the art have modified the expandable Z-stent to form eyes at the bends or joints of the zig-zag configuration. A monofilament line is then threaded through each of the eyes at one end of the stent to form, in essence, a continuous flexible ring which restricts the expansion of the wire stent. The monofilament line is sufficiently elastic in the tensile direction to control the expansion of the stent to an optimal desired diameter.

Further description of this modified expandable wire Z-stent is found in the following references:

Modified Gianturco Expandable Wire Stents in Experimental and Clinical Use, J. Rosch, CIRSE, Porto Cervo, Sardinia, May 25-29, 1987, Vol 31-No. 2, 1988

Modifications of Gianturco Expandable Wire Stents, Barry T. Uchida, AJR 150:1185-1187, May 1988, American Roentgen Ray Society Experimental Intrahepatic Portacaval Anastomosis: Use of Expandable Gianturco Stents, Josef Rosch, M.D., RSNA, 1987, Volume 162 No. 2

Superior Vena Cava Syndrome Associated with Massive Thrombosis: Treatment with Expandable Wire Stents, RSNA, June 1988

Gianturco Expandable Wire Stents in the Treatment of Superior Vena Cava Syndrome Recurring After Maximum-Tolerance Radiation, Reprinted from CANCER, Vol. 60, No. 6, Sept. 15, 1987.

There remains, however, a need for a percutaneous stent that is self-expanding, yet can be retrieved after a period of time of insertion. There is also need for a percutaneous stent that includes several stent sections for insertion along a greater length of a body passageway than has been permitted by expandable stents of the prior art. There is also a need for a stent capable of combination with multiple stent sections that does not require multiple catheterizations for insertion operations.

SUMMARY OF THE INVENTION

One embodiment of the self-expanding stent of the present invention includes a wire formed into a closed zig-zag configuration defining an endless series of straight sections joined by bends. At each of the bends is formed an eye which can be used for connection of another similarly constructed self-expanding stent, or for connection of a skirt stent of like construction. A number of self-expanding stents can be combined by joining the stents at the eyes. Each of the stents is resiliently compressible into a first smaller shape for insertion into a body passageway, such as through an introducer sheath. Once within the body passageway, the stents are resiliently expandable into a larger second shape wherein the straight sections press against the walls of the passageway to maintain it open.

Another embodiment of the invention involves a self-expanding stent of closed zig-zag configuration having eyes at bends joining the straight sections of the stent. A monofilament thread is passed through each of the eyes at one end of the stent, once through each of the eyes in a 360° loop and then again 180° through some of the eyes. The trailing free ends of the monofilament leave the stent at opposite sides of the stent diameter and extend through an introducer sheath outside the body passageway. The monofilament can be tied externally to limit the expansion of the self-expanding stent within the body passageway.

The free ends of the monofilament can also be used to reduce the diameter of the stent to permit retrieval of the stent from the body passageway. Thus, in a method of the invention, a tube is threaded over the free ends of the monofilament and advanced along the passageway until the tube is adjacent the expanded stent. The free ends are then pulled thereby contracting the outer diameter of the stent until the diameter is approximately equal to the diameter of the tube. A sheath can then be introduced over the tube and over the reduced diameter portion of the stent to further collapse the remaining length of the stent. The entire assembly, including the tube, sheath, stent and monofilament can then be removed from the body passageway.

One object of the invention is to provide a self-expanding stent that permits the combination of several interlocked stents for insertion into a body passageway. Another object of the invention is to provide a method for removal of a self-expanding stent situated within a body passageway. Other objects and benefits of the present invention can be discerned from the following written description of the invention along with the accompanying drawings.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3:
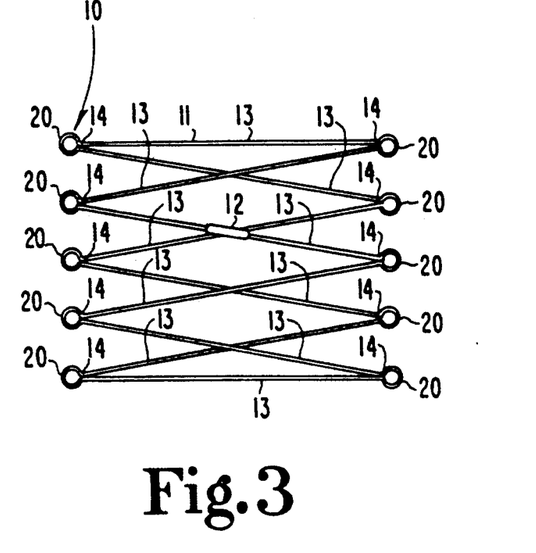
FIG. 3 is a side elevational view of a preferred embodiment of the present invention.
Figure 4:
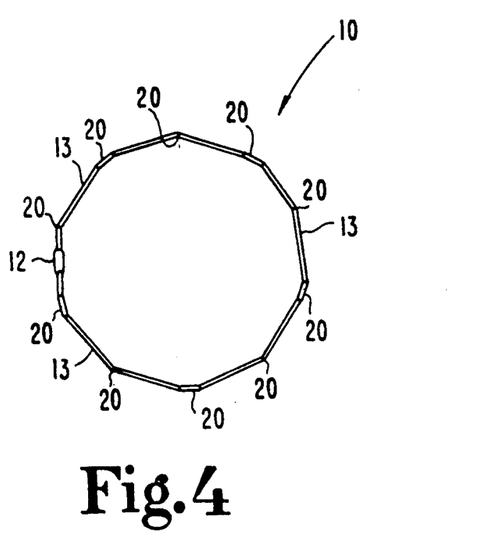
FIG. 4 is an end elevational view of the structure of FIG. 3.

Referring now more particularly to the drawings, there is illustrated in FIGS. 3-4 a side elevation of a preferred embodiment of the percutaneous stent 10 which is formed from a length 11 of stainless steel wire formed in a closed zig-zag configuration. The ends of the wire are closed by a sleeve 12 which is welded or tightly squeezed against the ends of the wire to produce a continuous or endless configuration. The length 11 of wire is arranged in a number of side-by-side straight sections 13. Adjacents straight sections 13 of the stents are adjoined by cusps 14.

Up to this point, the stent 10 of the present invention is, in most respects, similar to the Z-stent described in U.S. Pat. No. 4,580,568, which description is incorporated herein by reference. In particular, the specific embodiment of the invention includes the wire 11 which is of stainless steel having a 0.018 inch outer diameter. The cusps 14, that is the joint between adjacents straight sections 13, generally circumscribes a radius of no more than 0.2 cm or about 0.08 inch. As thus configured, the stent 10 is capable of being compressed into a relatively much smaller outer diameter than that shown in FIGS. 3-4, in order to permit insertion of the stent into the body passageway by use of a catheter or sheath.

In one novel aspect of the present invention, the cusps 14 of the stent are formed into a number of eyes 20. In the preferred embodiment, the eyes are formed in the continuous wire 11 and the intersection between adjacent straight sections 13 at the cusps 14 are soldered or welded together to provide a closed loop for the eyes 20. In one specific embodiment of the invention, the eyes have a diameter of approximately three times the wire diameter, or about 0.054 inch.

Figure 5:
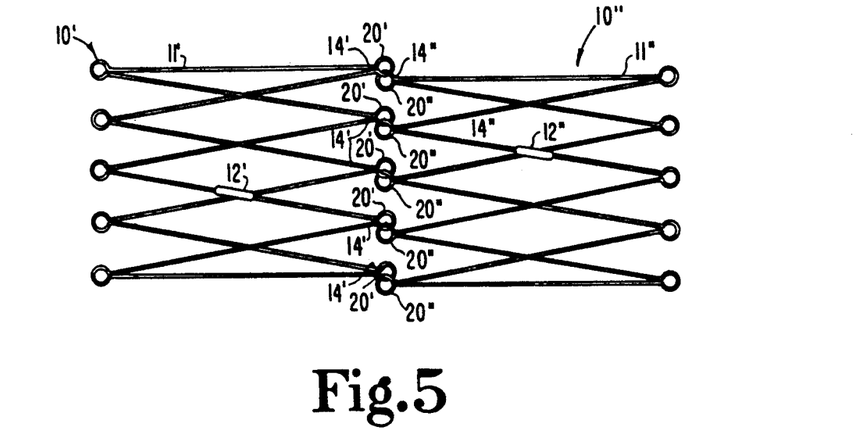
FIG. 5 is a side elevational view of another embodiment of the present invention.
Figure 6:
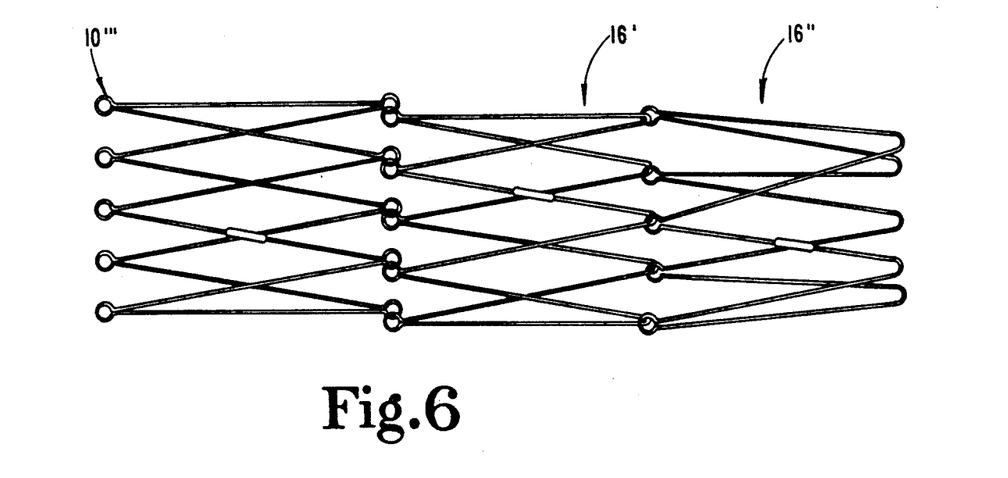
FIG. 6 is a side elevational view of another embodiment of the present invention.

In another embodiment of the invention, multiple stents are combined as shown in FIGS. 5 and 6. In the embodiment of FIG. 5, two self-expanding stents 10' and 10" are connected or attached at the eyes 20' and 20" at the ends of each of the stents. Each of the stents 10' and 10" are generally identical to the stent 10 just described. In constructing the union between the two stents 10' and 10", the first stent 10' is formed from a single length of stainless steel wire 11'. The length of wire 11' is formed into the zig-zag and eye configuration although the cusps 14' are not immediately soldered. The free ends of the length of wire 11' are joined by way of the sleeve 12'. Once the first stent 10' has been formed, the second stent 10" is formed from a second length 11" of stainless steel wire. The second length 11" is formed into the zig-zag and eye configuration so that the eyes 20" formed at one end of the stent are interlocked with the eyes 20' of the first stent 10'. Once the second stent 10" is complete, a sleeve 12" is used to connect the ends of the length of wire 11' and the cusps 14' and 14" can then be joined or soldered.

A similar method of construction can be used to interconnect a stent 10''', which is identical to the stent 10 described above, with a single skirt stent 16', as shown in FIG. 6. In this particular embodiment, the single skirt stent 16' does not have a number of eyes defined at the free end of the skirt. The free end of the skirt 16' may be formed into the configuration of hooks to prevent migration of the stent and skirt combination once the combination is placed within the body passageway. It is understood that in the embodiments of FIGS. 5 and 6, the eyes at one end of one stent or skirt may be connected to a stent having only bends or cusps at its connecting end, in a manner similar to the connection between skirt 16' and a similar skirt 16" shown in FIG. 6.

Figure 7A:
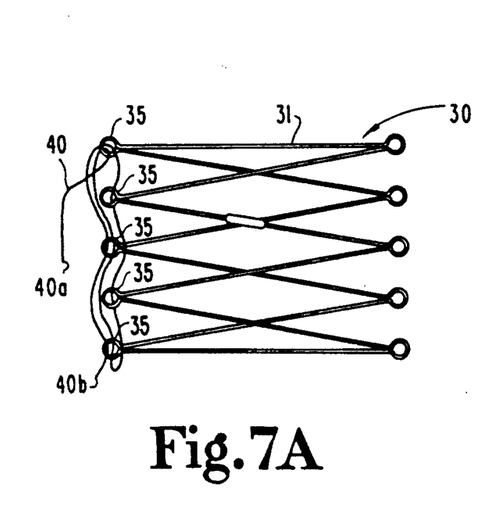
FIG. 7A is a side elevational view of still another embodiment of the present invention shown in its expanded state.
Figure 7B:
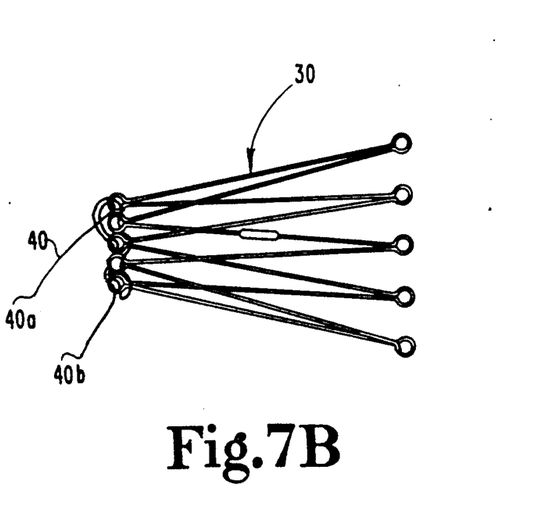
FIG. 7B is a side elevational view of the structure of FIG. 7A shown with one end in its contracted state.

In another embodiment of the present invention, a stent 30 is formed from a length of wire 31 into a zig-zag configuration identical to the stent 10 shown in FIG. 3. Alternatively, the stent 30 can be connected to a second stent, as shown in FIG. 5, or to a skirt, as shown in FIG. 6. A number of eyes 35 are formed at least at one end of the stent 30. A thread 40, preferably a monofilament of bio-compatible material, is passed through successive eyes around the circumference of the expanded stent 30. The thread 40 is passed through the eyes 35 by first passing one end 40a through each successive eye 35 while retaining the other end 40b outside and apart from the stent 30. The first end 40a of the thread 40 is threaded once through each of the eyes 35 in a 360° loop and then 180° further through successive eyes, or about 540° around the circumference of the stent, so that some of the eyes 35 will have two passes of the thread 40 therethrough. Thus, as shown in FIG. 7A, the two free ends 40a and 40b of the thread 40 are situated at 180° opposite eyes 35 of the stent 30. The thread 40 can then be used to collapse one end of the self-expanding wire stent by pulling both free ends 40a and 40b of the thread 40. When the free ends 40a and 40b are pulled simultaneously, the diameter of the thread 40, and therefore the diameter of one end of the stent 30, is decreased. Alternatively, the thread 40 can be used to limit the expanded diameter of the stent by tying the free ends 40a and 40b directly adjacent the stent.

Figure 8:
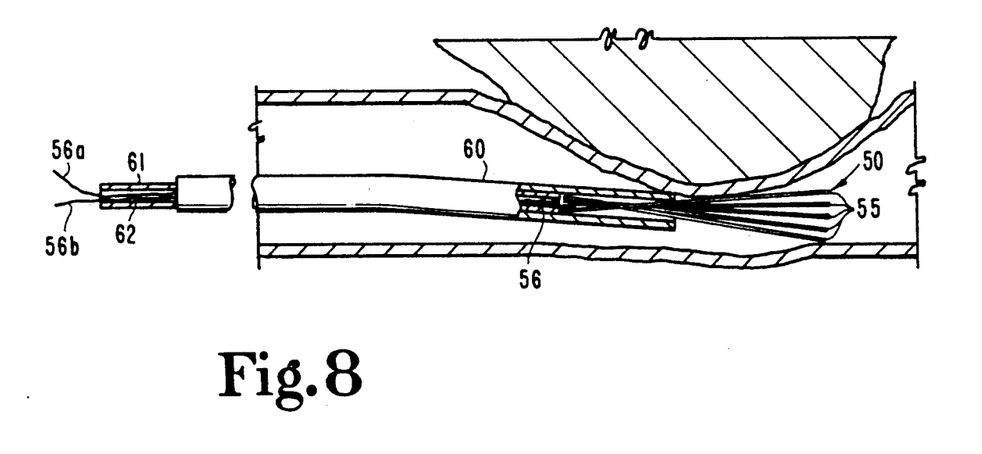
FIG. 8 is a sectional view of a body passageway showing a method of insertion of the self-expanding stent of the present invention.

In using the percutaneous stent of the present invention, an insertion technique similar to that described in the Gianturco '568 patent is employed, as shown in FIG. 8. A self-expanding stent 50 includes a number of eyes 55 at each end of the stent 50 and is identical in all respects to the stent 30 shown in FIG. 7A. The monofilament thread 56 passes through the eyes 55 at one end of the stent 50. In the method of insertion, the stent is compressed to its reduced diameter and disposed within a sheath 60, as shown in FIG. 8. The free ends 56a and 56b of the filament 56 extend outside the sheath 60 and exterior to the patient's body for access after the stent has been inserted. For example, when the stent is used as a prostatic stent, the filament 56 has a length of 30 to 40 cm measured from the stent 50 to each of the free ends 56a and 56b, so that the free ends may extend down from the prostate gland to the end of the urethra. When the stent 50 is used as a vascular stent, the length of the filament 56 may be considerably shorter, provided the ends 56a and 56b are situated outside the puncture site and are sufficiently long to be anchored onto the skin nearby.

Figure 9:
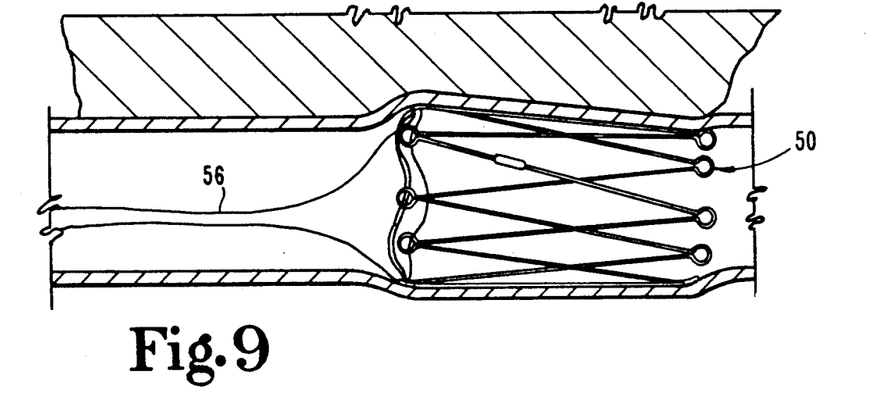
FIG. 9 is a sectional view of the body passageway similar to FIG. 8 following insertion of the self-expanding stent.

In the preferred embodiment, the free ends 56a and 56b of the filament 56 are tied together so that they can be easily controlled and maintained. When the stent 50 is compressed within the sheath 60, a pusher 61 is used to hold the stent 50 in position when the body passageway while the sheath 60 is withdrawn. The pusher 61 may have a channel 62 within which the monofilament 56 can be disposed to prevent any pinching or tugging of the filament while the sheath 60 is being removed. Once the sheath is removed, the pusher 61 can also be removed so that the stent 50 remains in position within the body passageway as shown in FIG. 9. The monofilament 56 trails the stent and passes outside the body as described above.

Figure 10A:
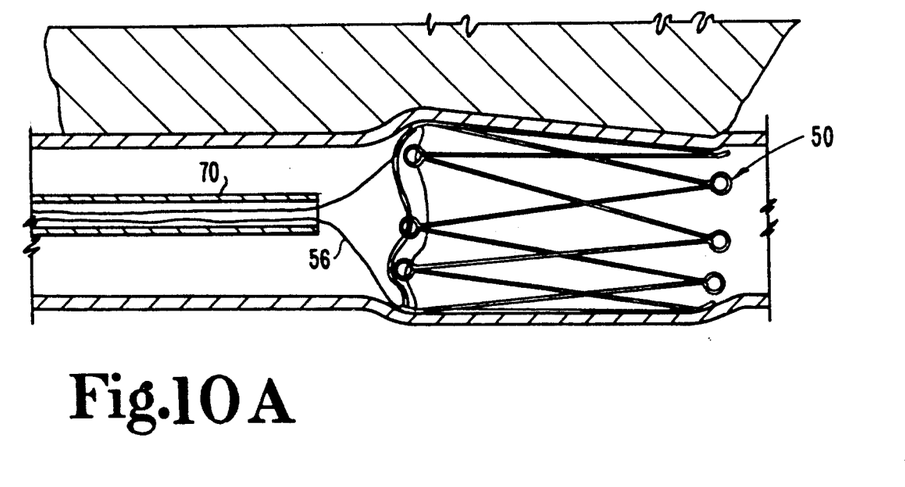
FIG. 10A is a sectional view of the body passageway shown in FIG. 9 showing one step of a method of retrieval of the self-expanding stent of one embodiment of the present invention.
Figure 10B:
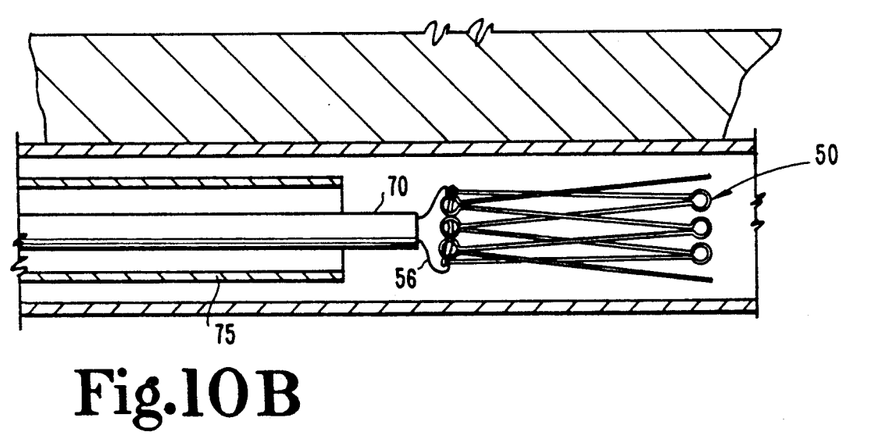
FIG. 10B is a view similar to FIG. 10A showing another step of the method of retrieval.
Figure 10C:
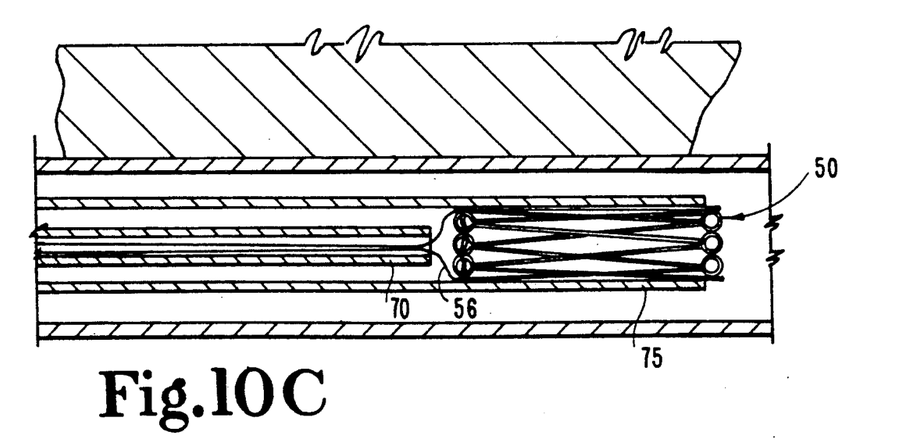
FIG. 10C is a view similar to FIG. 10B showing another step of the method of retrieval of the present invention.

In certain medical operations, the stent 50 need only be positioned temporarily within the body passageway. Thus, in another method of the present invention, illustrated with reference to FIGS. 10A-10C, the stent 50 is retrieved from the body passageway and removed. In the method of this embodiment, a tube 70 is threaded over the free ends of the monofilament 56 and inserted into the body passageway along the monofilament 56 until it is adjacent the implanted stent 50, as shown in FIG. 10A. Once the tube 70 is positioned directly adjacent the stent 50, the free ends of the monofilament 56 can be pulled through the tube 70, thereby compressing or contracting one end of the stent 50 to a reduced diameter, as shown in FIG. 10B. With the end of the stent 50 thus compressed, a sheath 75 can be introduced into the body passageway over the tube 70, as shown in FIG. 10C. The sheath 75 has an inner diameter larger than the reduced diameter of the end of the stent 50. The sheath 75 is continually conveyed into the body passageway over the tube 70 until it contacts and compresses the remaining length of the self-expanding stent 50. Once the sheath 75 completely covers or shrouds the stent 50, that is when the stent 50 is disposed entirely within the sheath 75, the entire assembly can be removed from the body passageway. In the preferred embodiment of the present method, the tube 70 and sheath 75 are composed of medical grade plastic, such as an 8-polyethylene tubing.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A stent assembly comprising:
  a first wire formed into a closed zig-zag configuration including;
    an endless series of straight sections having opposite ends, said straight sections being joined by bends at said opposite ends to form a stent;
    a set of eyes formed at several of said bends at one of said opposite ends; and
  a thread passing through successive ones of said set of eyes, said thread including a pair of free ends trailing from said stent;
  wherein said stent is resiliently contractable into a smaller first shape for conveyance through a body passageway;
  wherein said one end of said stent is contractable by drawing said pair of free ends of said thread;
  wherein said stent is resiliently expandable into a second shape in which the straight sections press against the walls of the body passageway; and
  wherein said free ends are sufficiently long to extend outside the body passageway when said stent is situated within the passageway.

2. The stent assembly of claim 1, wherein:
  said second shape of said stent includes a circumference at said one of said opposite ends, said set of eyes being situated at said circumference; and
  said thread passes through successive eyes at least 360° around said circumference.

3. The stent assembly of claim 2, wherein said thread passes through successive eyes approximately 540° around said circumference.

4. The stent assembly of claim 1, further comprising:
  a second wire formed into a closed zig-zag configuration including;
    a second endless series of straight sections having opposite ends, said straight sections being joined by bends at said opposite ends to form a second stent;
    a second set of eyes formed at several of said bends at one of said opposite ends;
  wherein said second stent is resiliently contractable into a smaller first shape for conveyance through a body passageway;

wherein said second stent is resiliently expandable into a second shape in which the straight sections press against the walls of the body passageway; and wherein said second set of eyes of said second wire are engaged about said first wire at one of said opposite ends.

5. The stent assembly of claim 4, wherein:

said first wire includes a third set of eyes formed at several bends at the other of said opposite ends of said first wire; and said second set of eyes of said second wire are interengaged with said third set of eyes.

6. A method for combining a first and second self-expanding stent to form a stent assembly for insertion into a body passageway comprising the steps of:

forming a first stent from a continuous first length of wire formed into a closed zig-zag configuration having an endless series of straight sections joined at their ends by a plurality of bends;

forming a second stent from a continuous second length of wire formed into a closed zig-zag configuration having an endless series of straight sections joined at their ends by a plurality of bends, the bends at one end defining eyes open at the straight sections of the second stent;

engaging the eyes at the one end of the second stent about bends at one end of the first stent; and closing the eyes at the one end of the second stent.

7. The method of claim 6 wherein:

the step of forming the first stent includes forming eyes at the one end of the first stent, the eyes open at the straight sections of the first stent; and the step of engaging the eyes at one end of the second stent includes interlocking the eyes of the second stent with the eyes of the first stent and closing the eyes at the one end of the first stent.

8. A method for retrieving a stent disposed within a body passageway, the stent including a resilient wire formed in a closed zig-zag configuration having a set of eyes formed at one end of the stent, with a thread passing through successive eyes of the stent and having two free ends trailing from the stent outside the body passageway, the stent having a first compressed shape and a second expanded shape in which the resilient wire contacts the wall of the body passageway, comprising the steps of:

pulling the free ends of the thread to reduce the diameter of the one end of the stent while maintaining the position of the stent within the body passageway;

reducing the diameter of the remainder of the stent sufficient to permit travel of the stent through the body passageway;

retracting the compressed stent through the passageway.

9. The method for retrieving a stent of claim 8, wherein said step of pulling the free ends further includes the steps of:

threading a tube over the trailing free ends of the thread, the tube having an inner diameter smaller than the diameter of the first compressed shape of the stent;

introducing the tube into the body passageway and conveying the tube to a position adjacent the stent;

pulling the free ends of the thread through the tube to reduce the diameter of the one end of the stent.

10. The method for retrieving a stent of claim 9, wherein said step of reducing the diameter of the remainder of the stent further includes the steps of:

introducing a sheath concentrically disposed over the tube into the body passageway;

conveying the sheath over the tube through the body passageway and over the reduced diameter end of the stent;

further conveying the sheath over the remainder of the stent to compress the remainder of the sheath and withdraw the stent from contact with the wall of the body passageway.

11. The method for retrieving a stent of claim 8, wherein said step of reducing the diameter of the remainder of the stent further includes the steps of:

threading a sheath over the trailing free ends of the thread, the sheath having an inner diameter larger than the diameter of the first compressed shape of the stent but smaller than the diameter of the second expanded shape of the stent;

introducing the sheath into the body passageway and conveying the sheath through the body passageway and over the reduced diameter end of the stent;

further conveying the sheath over the remainder of the stent to compress the remainder of the sheath and withdraw the stent from contact with the wall of the body passageway.

12. A stent assembly comprising:

a first wire formed into a closed zig-zag configuration including;

an endless series of straight sections having opposite ends, said straight sections being joined by bends at said opposite ends to form a first stent; and a second wire formed into a closed zig-zag configuration including;

a second endless series of straight sections having opposite ends, said straight sections being joined by bends at said opposite ends to form a second stent;

a set of eyes formed at several of said bends at one of said opposite ends;

wherein said first and second stents are resiliently contractable into a smaller first shape for conveyance through a body passageway;

wherein said first and second stents are resiliently expandable into a second shape in which the straight sections press against the walls of the body passageway; and wherein said set of eyes of said second stent are engaged about said first wire at one of said opposite ends of said first wire.

* * * * *

UNITED STATES PATENT AND TRADEMARK OFFICE
CERTIFICATE OF CORRECTION

PATENT NO. : 5,035,706

DATED : July 30, 1991

INVENTOR(S) : Cesare Gianturco et al.

It is certified that error appears in the above-identified patent and that said Letters Patent is hereby corrected as shown below:

On the title page, under item [19] and in item [75]:
The inventor's name should be changed from "Giantureo" to --Gianturco--.

Signed and Sealed this

Third Day of November, 1992

Attest:

DOUGLAS B. COMER

*Attesting Officer*  Acting Commissioner of Patents and Trademarks

(12) EX PARTE REEXAMINATION CERTIFICATE (7458th)
United States Patent
Gianturco et al.

(10) Number: US 5,035,706 C1
(45) Certificate Issued: Apr. 20, 2010

(54) PERCUTANEOUS STENT AND METHOD FOR RETRIEVAL THEREOF

(75) Inventors: Cesare Gianturco, Champaign, IL (US); Thomas A. Osborne, Bloomington, IN (US)

(73) Assignee: Cook Incorporated, Bloomington, IN (US)

Reexamination Request:
No. 90/010,748, Nov. 23, 2009

Reexamination Certificate for:
Patent No.: 5,035,706
Issued: Jul. 30, 1991
Appl. No.: 07/422,606
Filed: Oct. 17, 1989

Certificate of Correction issued Nov. 3, 1992.

(51) Int. Cl.
*A61M 29/00* (2006.01)

(52) U.S. Cl. .................................................. 606/198
(58) Field of Classification Search .................. None
See application file for complete search history.

(56) References Cited

U.S. PATENT DOCUMENTS

| | | |
|---|---|---|
| 3,498,335 A | 3/1970 | Cook |
| 4,994,071 A | 2/1991 | MacGregor |
| 5,019,090 A | 5/1991 | Pinchuk |
| 5,133,732 A | 7/1992 | Wiktor |

OTHER PUBLICATIONS

Uchida, et al, Modifications of Gianturco Expandable Wire Stents, AJR: 150, pp. 1185–1187, May 1988.

*Primary Examiner*—Jeanne M Clark (57) ABSTRACT

A self-expanding stent formed of stainless steel wire arranged in a closed zig-zag configuration includes an endless series of straight sections joined at their ends by bends. The stent is compressible into a reduced diameter size for insertion into and removal from a body passageway. The bends of at least one end of the stent are formed into eyes for connection with the eyes at one end of a similarly constructed stent to permit single-step introduction of several lengths of stent into the passageway. A stent can include a monofilament thread passing through successive eyes at one end of the stent, the thread passing through each eye at least once and through some of the eyes a second time. The trailing ends of the thread extend from the stent and outside the body passageway. The stent can be retrieved from the body passageway by threading a tube of the free ends of the thread until the tube is adjacent the stent. The diameter at one end of the stent is reduced by pulling the free ends of the thread through the tube. A sheath concentrically disposed over the tube is introduced into the body passageway and over the remaining length of the stent to further compress the stent for removal from the passageway.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 6 and 12 is confirmed.

Claims 1–5 and 7–11 were not reexamined.

\* \* \* \* \*